United States Patent
Fujii

(10) Patent No.: US 7,306,579 B2
(45) Date of Patent: Dec. 11, 2007

(54) NEEDLELESS PORT

(75) Inventor: Ryoji Fujii, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 0 days.

(21) Appl. No.: 10/524,195

(22) PCT Filed: Aug. 11, 2003

(86) PCT No.: PCT/JP03/10194

§ 371 (c)(1),
(2), (4) Date: Feb. 10, 2005

(87) PCT Pub. No.: WO2004/020037

PCT Pub. Date: Mar. 11, 2004

(65) Prior Publication Data

US 2005/0256500 A1    Nov. 17, 2005

(30) Foreign Application Priority Data

Aug. 12, 2002 (JP) .............................. 2002-235170

(51) Int. Cl.
*A61M 5/00* (2006.01)
(52) U.S. Cl. ...................... 604/244; 604/256
(58) Field of Classification Search .............. 604/244, 604/82, 86, 90, 167.01, 905, 256, 167.02
See application file for complete search history.

(56) References Cited

U.S. PATENT DOCUMENTS

| | | | |
|---|---|---|---|
| 2,328,948 A * | 9/1943 | Bourke | 217/103 |
| 3,517,682 A * | 6/1970 | Smith | 137/68.23 |
| 4,434,810 A * | 3/1984 | Atkinson | 137/493 |
| 4,612,960 A * | 9/1986 | Edwards et al. | 137/846 |
| 5,010,925 A * | 4/1991 | Atkinson et al. | 137/847 |
| 5,178,607 A * | 1/1993 | Lynn et al. | 604/86 |
| 5,199,948 A * | 4/1993 | McPhee | 604/86 |

(Continued)

*Primary Examiner*—Kevin C. Sirmons
*Assistant Examiner*—Andrew Gilbert
(74) *Attorney, Agent, or Firm*—Hamre, Schumann, Mueller & Larson, P.C.

(57) ABSTRACT

A septum (1) is held in the cavity of a cover (6) and mounted on a pedestal (7) forming part of a flow channel, and comprises a main body having a through passageway and compression ribs formed in the sides thereof. In the main body, the vertical diameter of the cross section orthogonal to the through passageway is longer than the transverse diameter, and the through passageway includes a vertical diameter direction slit (4) formed in the vicinity of the outer end surface of the main body, and a hole (5) that is formed in a region extending from the slit to the inner end surface of the main body and whose cross section is spindle-shaped having a longer axis extending in the vertical diameter direction. The compression ribs are formed in the opposite sides of the main body in the transverse diameter direction, and the cavity of the cover is of circular cross section whose diameter is shorter than the outer surface spacing between the compression ribs. With the septum mounted, a space is defined between part of the surface of the main body and the inner wall surface of the cover. Further, the hole is closed by a compressive force acting on the septum from the inner wall surface of the cover through the compression ribs. The through passageway in the septum hardly forms a dead space that would cause a residual liquid therein, and the slit in the septum surface hardly opens even at the time of pressurization.

22 Claims, 11 Drawing Sheets

U.S. PATENT DOCUMENTS

| | | | |
|---|---|---|---|
| 5,203,775 A * | 4/1993 | Frank et al. | 604/256 |
| 5,301,707 A * | 4/1994 | Hofsteenge | 137/12 |
| 5,354,275 A | 10/1994 | Behnke et al. | |
| 5,470,319 A * | 11/1995 | Mayer | 604/167.02 |
| 5,474,544 A | 12/1995 | Lynn | |
| 5,533,708 A * | 7/1996 | Atkinson et al. | 251/149.1 |
| 5,699,821 A | 12/1997 | Paradis | |
| 6,089,541 A * | 7/2000 | Weinheimer et al. | 251/149.6 |
| 6,171,287 B1 * | 1/2001 | Lynn et al. | 604/256 |
| 6,767,340 B2 * | 7/2004 | Willis et al. | 604/256 |
| 6,908,459 B2 * | 6/2005 | Harding et al. | 604/533 |
| 7,033,339 B1 * | 4/2006 | Lynn | 604/256 |
| 7,037,303 B2 * | 5/2006 | Beaufore et al. | 604/537 |
| 2004/0102738 A1 * | 5/2004 | Dikeman et al. | 604/256 |

\* cited by examiner

NEEDLELESS PORT

TECHNICAL FIELD

The present invention relates to a needleless port that is provided on a flow channel for liquid medicine and the like and into which a dull needle such as luer can be inserted, and relates to a method of manufacturing such a needleless port.

BACKGROUND ART

In recent years, in view of preventing infection due to accidental needle stick, dull needles (hereafter, also referred to as luers or the like) have come into wide use as alternatives for sharp metal needles that have been used conventionally. Such a dull needle is used in combination with a port (hereafter, it will be referred to as a needleless port) into which the dull needle can be inserted, and the combination of a dull needle and a port is specially adapted.

When only a certain kind of luers can be exclusively used with a particular kind of needleless ports, those luers cannot be used for the containers and bags that have other kinds of ports, and do not have very high compatibility.

When it is difficult to have a luer syringe securely held after insertion, a luer lock syringe sometimes is used instead. There have been developments of needleless ports that each have such a structure into which any types of luer syringes and luer lock syringes that meet the normal ISO standards can be inserted. For example, the U.S. Pat. No. 6,089,541 discloses a port in which a deformable septum is disposed so as to be shiftable inside the main body, and the internal structure of the septum, besides the opening, is a hollow. When an insertion member such as a luer is inserted into the opening of the septum, liquid communication is established. In addition, in order to make it possible to insert a luer lock syringe as well, a male screw-thread for screw-fastening is provided in the vicinity of the opening of the main body.

The U.S. Pat. No. 5,699,821 discloses a port in which a deformable, oblong, and tube-shaped septum is disposed inside the main body so as to be slidable. When an insertion member such as a luer is inserted into the opening of the septum, liquid communication is established. The oblong, tube-shaped septum has a passageway therethrough, and in the natural state, i.e. before the septum is mounted in the main body of the port, the passageway is open. When the septum is mounted in the main body, the function as a septum is exerted by having the entrance (or the exit) compressed. In addition, in order to make it possible to insert a luer lock syringe as well, a male screw-thread for screw-fastening is provided in the vicinity of the opening of the main body.

The U.S. Pat. No. 5,474,544 discloses a port in which a deformable septum is mounted inside the main body so as to be expandable. When an insertion member such as a luer is inserted into the opening of the septum, liquid communication is established and the port is filled with the septum having been deformed, thereby preventing fluid leaks. In addition, in order to make it possible to insert a luer lock syringe as well, a male screw-thread for screw-fastening is provided in the vicinity of the opening of the main body.

The conventional needleless ports mentioned above, however, each have a complicated structure and it is difficult to eliminate the dead space therein. Since there is a space in which bubbles can remain, safety during blood transfusion or infusion has not been sufficient.

For example, a septum disclosed in the U.S. Pat. No. 6,089,541, has a hollow internal structure besides the opening, and the hollow acts as a dead space. It is difficult to remove the bubbles remaining in this dead space.

The deformable septum disclosed in the U.S. Pat. No. 5,699,821 is oblong and tube-shaped and therefore, there is a hollow between the entrance and the exit, which acts as a dead space. It is difficult to remove the bubbles remaining in the space.

As for the septum disclosed in the U.S. Pat. No. 5,474,544, when the septum is deformed inside the main body, the septum tends to have a hollow therein, and it is difficult to completely avoid formation of a dead space. Further, it is difficult to balance avoidance of a dead space with easiness of insertion of a luer or the like.

Among these difficulties, focusing especially on avoiding formation of a dead space, the U.S. Pat. No. 5,354,275 discloses an injecting unit that is to be used with a septum having a slit or a through hole and makes it possible to completely avoid formation of a dead space by structurally solving the problem of having a hollow when a luer or the like is inserted. The injecting unit, however, may cause the following problems.

In the structure disclosed in the U.S. Pat. No. 5,354,275, in which the septum has a through hole, when a pressure is applied to the inside thereof and the septum is pressed upward, since the hole is open in the normal state, the hole on the surface of the septum tends to open up easily. Thus, there is a possibility that airborne bacteria and the like stick to the open hole and the inside of the septum is contaminated.

In the structure disclosed in the U.S. Pat. No. 5,474,544, although the septum has a slit therethrough, no additional compressive force is applied in the direction orthogonal to the slit. In such a structure, since the slit is not compressed, there is a possibility that medicinal fluid or the like remains in the slit. In addition, it is difficult to provide a slit at an accurate position in a septum that has a large thickness.

As for the structures disclosed in the U.S. Pat. No. 6,089,541 and 5,699,821, the internal structure is a hollow besides the opening. It is difficult to perform a priming process with such a structure, and there is a possibility that remaining air that has not been removed in the priming process may be pushed into the tubes during a process of supplying mixed injections. Also, when injected liquid medicine remains in the structure, it is difficult to measure exactly how much medicine has been injected to a patient. Further, when blood is in the main tube, there is a possibility that thrombi are caused due to the stagnation inside the hollow area.

DISCLOSURE OF THE INVENTION

It is an object of the present invention to provide a needleless port in which formation of a dead space inside a passageway in a septum causing a residual fluid is suppressed, and in which the slit provided on the surface of the septum does not open easily even when a pressure is applied.

A needleless port according to an embodiment of the present invention includes: a pedestal that forms a part of a flow channel and has an opening to the flow channel; a cover that is engaged with the pedestal at a position corresponding to the opening and has a cavity that opens to exterior at a predetermined distance from the opening; and a septum that is held in the cavity and is made of a resilient material with a passageway for allowing an insertion member to be inserted from the exterior to the opening.

In order to achieve the object, the septum includes: a main body that extends from an inner end on the pedestal side toward an outer end on the exterior side of the cavity of the cover, with the passageway being formed between an inner-end face and an outer-end face thereof, and compression ribs provided on sides of the main body. The main body has a cross section in a direction orthogonal to the passageway of a shape having a dimension in a length direction larger than that in a breadth direction. The passageway includes a slit and a bore, the slit having a predetermined depth from the outer-end face of the main body and extending in the same direction as the length direction, and the bore extending from the slit to the inner-end face of the main body and having a lateral section of a spindle shape whose major axis extends in the same direction as the length direction. The compression ribs are provided at the both side ends of the main body in the breadth direction so as to extend along the axial direction of the passageway. The cavity of the cover has a circular cross section whose diameter is smaller than a distance between the external surfaces of the compression ribs.

With the septum being held inside the cavity, a space is formed between an external surface of the main body at a part without the compression ribs and an internal wall of the cover, and the bore is closed by a compressive force applied from the internal wall of the cover to the septum via the compression ribs.

The needleless port according to another embodiment of the present invention has the same configuration as above, except that the septum has a substantial passageway that potentially allows an insertion member to go through, instead of the passageway that is completely penetrating. The substantial passageway includes an unpenetrated region and a bore, the unpenetrated region having a predetermined depth from the outer-end face of the main body, and the bore extending from the unpenetrated region to the inner-end face of the main body and having a lateral section of a spindle shape whose major axis extends in the same direction as the length direction.

A method of manufacturing the needleless port according the present invention provides a method of manufacturing the needleless port with the above-mentioned configurations, wherein in a process of molding the septum, a knob is formed on the outer-end face of the septum at a position being displaced from a position of the slit, and when mounting the septum inside the cavity, the knob is put through the cavity from the inner end thereof to the outer end thereof and thereafter the knob is pulled while the septum is pushed into the cavity.

BEST MODE FOR CARRYING OUT THE INVENTION

Figure 1A:
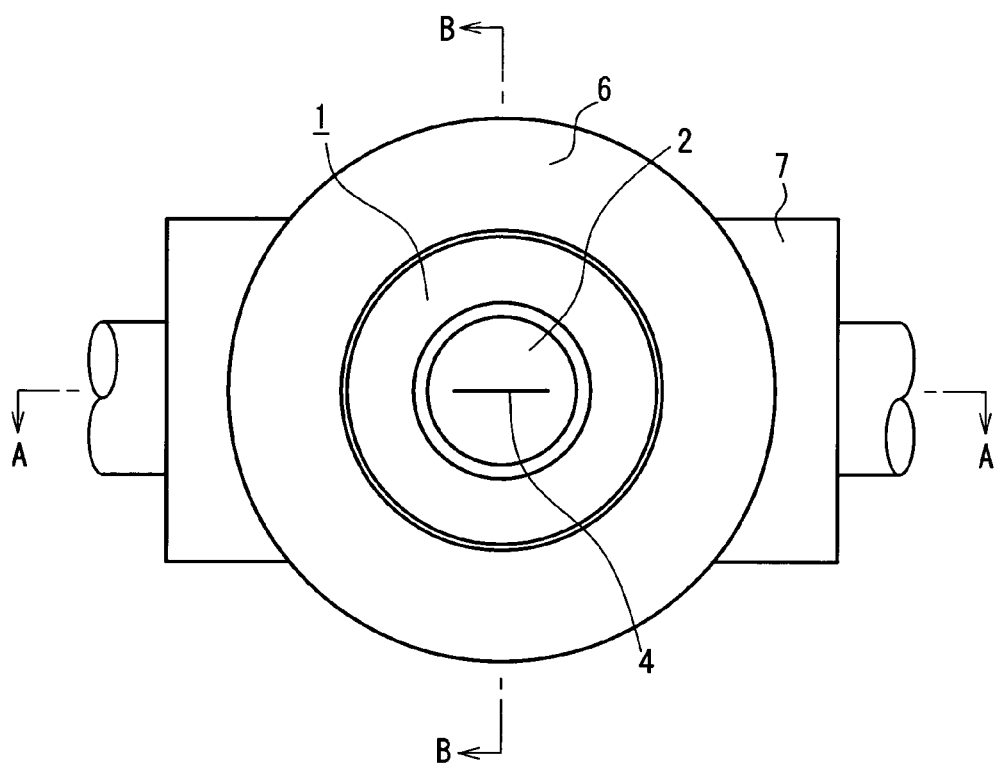
FIG. 1A is a plan view of the needleless port of an embodiment of the present invention and FIG. 1B is a cross sectional view thereof along a line A-A.

According to the needleless port of the present invention, since it employs the combination of the configuration in which the passageway is composed of the slit and the bore adjoined with each other and the configuration in which the compressive force is applied to the septum via the compression ribs so as to close the bore, it is possible at the same time to make it easy to insert an insertion member, to eliminate the dead space in the passageway of the septum, and to keep the integrity of the slit on the surface of the septum when a pressure is applied. That is, since there is a bore, it is easy to insert an insertion member, and further, since the compressive force is applied to the septum via the compression ribs so that the bore is closed, it is less likely that the bore creates a dead space. Further, even if the septum is pressed outward by an internal pressure, the septum hardly opens because it has a slit on the outer-end face thereof, instead of a bore.

The "slit" is defined as a path which is formed of a cut made into the material of the septum, and the walls of the cut are in contact to each other so that the path is closed, even when the septum is free and no force is applied thereto. The "bore" is defined as a path which is formed in the septum in such a state that the walls thereof are apart from each other so as to open the path when the septum is free and no force is applied thereto. The "spindle shape" is defined as a shape formed of two arcs combined symmetrically so that both ends are pointed.

In the septum composing the needleless port according to another embodiment of the present invention, the unpenetrated portion has substantially the same function as the slit. In other words, it is possible to break the unpenetrated portion with an insertion member, and the broken part functions substantially in the same manner as the slit.

In the needleless port of the above configuration, it is preferable that the septum has, on an inner end of the main body, an inner-end plate that has an oval shape whose major axis extends in the same direction as the breadth direction of the main body. A major axis of the inner-end plate is larger than an inside diameter of the internal wall of the cover, and with the septum being held inside the cavity, a compressive force acting in the major axis direction is applied from the cover to the inner-end plate. Thereby it is possible to ensure further that the compressive force is applied to the septum.

Further, it is preferable that the septum has, around an outer end of the main body, an outer-end plate that is exposed to outside of the cover and is larger in size than an inside diameter of the cover at an outer end of the cover. With this configuration, it is possible to prevent the septum from falling inside the cavity of the cover. Further, after an insertion member is taken out, it is easy to have the septum restored to the state before the insertion.

Further, it is preferable that lengths in the major axis and the minor axis of the section of the bore gradually become larger from the outer-end face of the main body toward the inner-end face of the main body. With this configuration, since the area size of a cross section of the bore gradually becomes larger towards the bottom thereof it is easy to put out remaining fluid, if any, from the bottom of the septum, with the restoration force of the septum.

Moreover, it is preferable that the septum has, on an outer end thereof a surface depression portion which is formed at a central area to be substantially level and depressed in relation to an area surrounding the central area. With this configuration, it is possible to guide an insertion member such as a luer into the passageway of the septum easily, as well as to disinfect the septum with an alcohol cotton ball.

Furthermore, it is preferable that a surface of the outer-end plate is flat. With this configuration, the septum has hardly any dead space on the inner end thereof.

Further, it is preferable that a length $Ls0$ of the main body in a state in which the septum is not mounted inside the cover is smaller than a length $Lc$ of the cover at a portion for holding the main body therein. With this configuration, since the main body of the septum expands, it is possible to accelerate the restoration of the outer-end plate when an internal pressure is applied.

Further, it is preferable that with the septum being held inside the cover, an expansion ratio is within a range of 5% to 40%, the expansion ratio being calculated by dividing an expanded length of the septum by the length $Lc$. When the expansion rate is smaller than 5%, the restoration force of the outer-end face of the septum is too weak. When the expansion rate is larger than 40%, as a result of an excessive load applied to the septum, the septum gets degraded, for example, the resilience of the septum is lowered, or in an extreme case, the septum tends to be damaged easily.

Further, it is preferable that the internal wall of the cover forming the cavity is tapered so that the diameter of the cavity section gradually becomes larger from the inner end thereof toward the outer end thereof along an axis of the cavity. With this configuration, when there is a force that acts so as to press the septum outward resulting from a pressure from the inside of the flow channel, it is possible to cause a counter force acting against such a force to be applied to the septum from the tapered wall of the cavity.

Further, it is preferable that a ratio of the distance between the external surfaces of the compression ribs to the inside diameter of the cover and a ratio of the length in the major axis of the inner-end plate to the inside diameter of the cover are each within a range of 1.05 to 1.4. It is also preferable that a ratio of a dimension in the breadth direction of the main body to the inside diameter of the cover and a ratio of a minor axis of the inner-end plate to the inside diameter of the cover are each within a range of 0.8 to 1.0. With these configurations, when the septum is pushed into the cover, it is possible to ensure that a compressive force is applied to the bore.

Further, it is preferable that an area size of a cross section of the space between the external surface of the main body at the portion without the compression ribs and the internal wall of the cover gradually becomes larger from an outer end of the cover toward an inner end of the cover. With this configuration, when an insertion member is inserted, it is possible to prevent the septum from being twisted.

Furthermore, it is preferable that a ratio of the predetermined depth of the slit to a height of the main body of the septum is within a range of 0.04 to 0.60, the predetermined depth being measured in a direction of the passageway. It is also preferable that the predetermined depth of the slit measured in a direction of the passageway is within a range of 0.2 mm to 3.0 mm. With these configurations, when the septum is slightly pressed upward due to an excessive internal pressure, it is possible to sufficiently prevent the slit provided on the upper end of the septum from opening up. When the ratio is smaller than 0.04, the effect of preventing the slit from opening up is insufficient. When the ratio is larger than 0.60, it is difficult to insert or to hold an insertion member such as a luer. When the depth of the slit is smaller than 0.2 mm, the aforementioned effect is insufficient. When the depth of the slit is larger than 3.0 mm, it is difficult to form the slit and to insert or to hold the insertion.

Further, it is preferable that an annular rib is provided around the opening of the pedestal, the annular rib projecting toward the cover, and the inner-end plate of the septum is sandwiched between the internal wall of the cover and the annular rib so that the annular rib engages with a bottom surface of the inner-end plate, thereby establishing liquid-tightness.

Further, it is preferable that the internal wall of the cover has one or more indents that are to be engaged with an external surface of the septum. With this configuration, even when a luer lock syringe is rotated, since the septum is engaged with the indents, the septum is unlikely to get twisted, and it is possible to maintain the passageway.

Further, it is preferable that an inner peripheral portion at an outer end of the cover is chamfered. With this configuration, even when insertion members are repeatedly inserted into and taken out from the needleless port, it is possible to prevent the inside peripheral portion on the outer end of the cover from damaging the septum at a part abutted by the portion, protecting the septum from damage.

It is acceptable that a material of the septum is one of silicon rubber, isoprene rubber, butyl rubber, nitrile rubber and thermoplastic elastomer.

According to a method of manufacturing a needleless port of the present invention, it is easy to mount the septum, because the knob formed at a position in the outer-end face of the septum is pulled while the septum is pushed into the cavity.

In this manufacturing method, after the septum is mounted inside the cavity, the knob may be cut off at a basal portion thereof.

It is preferable that the knob is tube-shaped, with the basal portion thereof being formed so as to surround the slit, and after the septum is pushed into the cavity, the tube-shaped knob is turned inside out so as to cover an external surface of the cover.

Figure 1B:
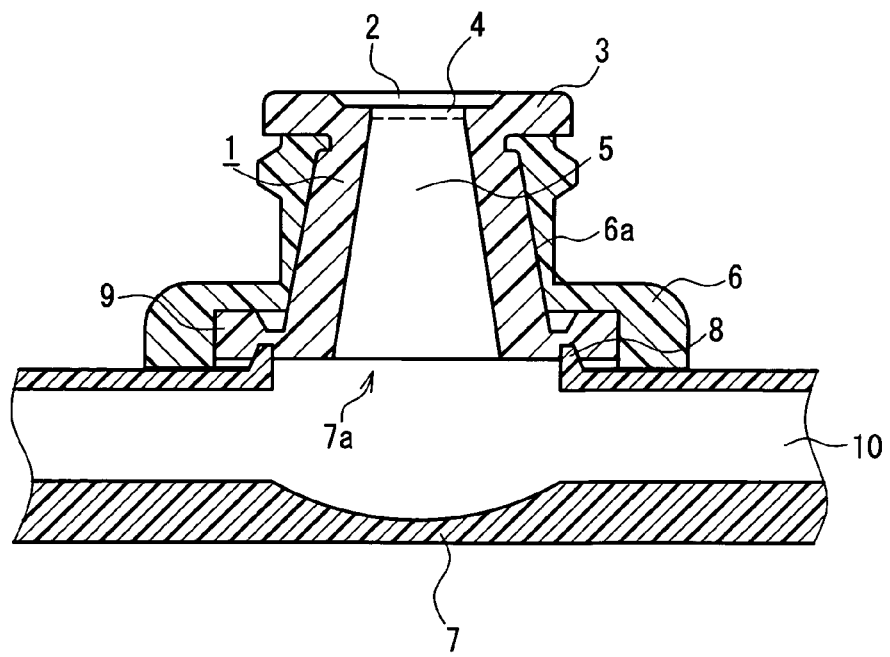
Figure 2:
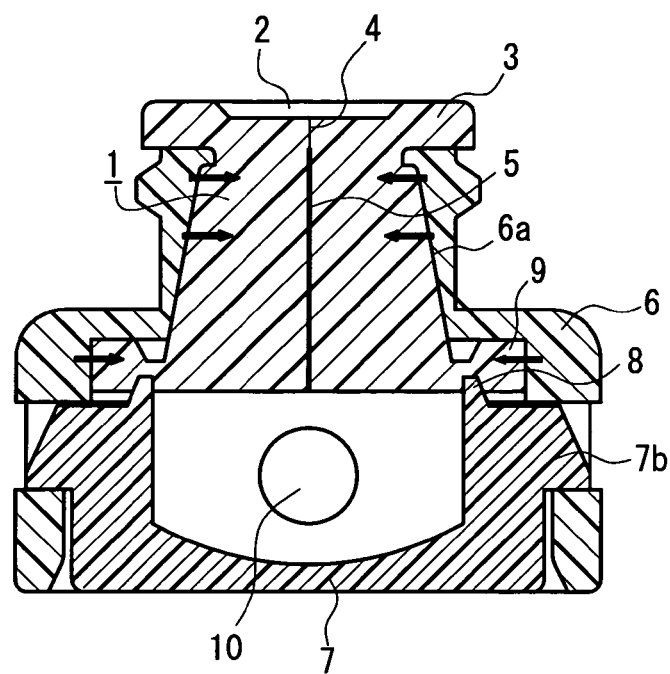
FIG. 2 is a cross sectional view along a line B-B in FIG. 1.

The following describes embodiments of the present invention more specifically, with reference to the drawings. FIG. 1A is a plan view of a needleless port of an embodiment of the present invention. FIG. 1B is a cross sectional view thereof along a line A-A in FIG. 1A. FIG. 2 is a cross sectional view thereof along a line B-B in FIG. 1A.

As shown in FIGS. 1A, 1B, and 2, a pedestal 7 forms a part of a flow channel 10 and has an opening 7a that opens to the flow channel 10. A cover 6 is attached to the pedestal 7 at a position that corresponds to the opening 7a. The cover 6 has a cavity 6a extending from the opening 7a in a lateral direction of the flow channel 10 so as to open to the exterior. A septum 1, which is made of a resilient material, is held in the cavity 6a.

The septum 1 has a surface depression 2 on the outer end thereof, with an outer-end plate 3, which is large in thickness, being formed around the surface depression 2. A slit 4 is provided on the surface of the outer end of the septum 1. A bore 5 is formed beneath the slit 4. It is possible to allow an insertion member such as a luer to be inserted from the exterior of the port to reach the opening 7a of the pedestal 7 through the passageway composed of the slit 4 and the bore 5.

An annular rib 8 is provided around the opening 7a of the pedestal 7 and projects toward the cover 6. An inner-end plate 9, which is large in thickness, is formed around the inner end of the septum 1 and is sandwiched between the cover 6 and the pedestal 7.

Figure 3:
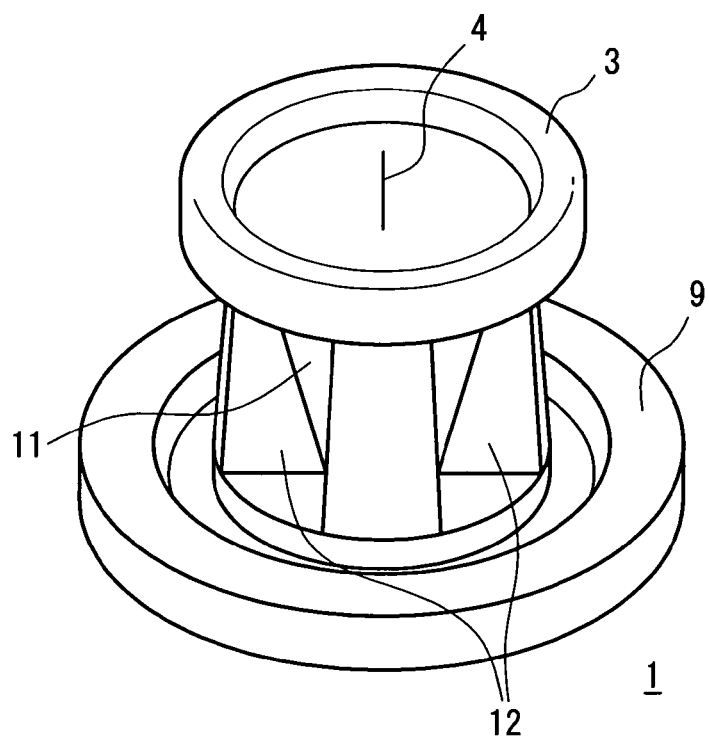
FIG. 3 is a perspective view of a septum as being mounted into the needleless port shown in FIG. 1.
Figure 4A:
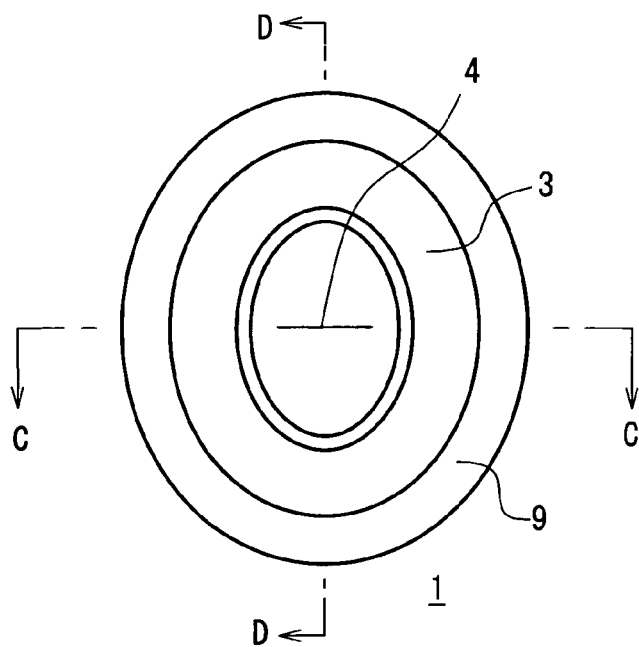
FIG. 4A is a plan view of the septum by itself to be mounted into the needleless port shown in FIG. 1.
Figure 4B:
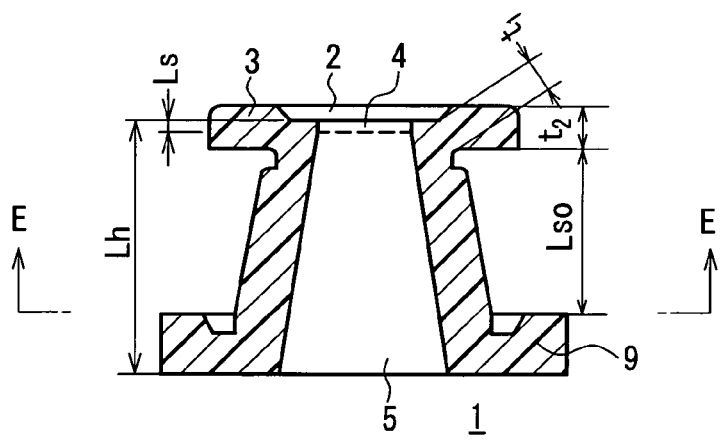
FIG. 4B is a cross sectional view thereof along a line C-C.
Figure 4C:
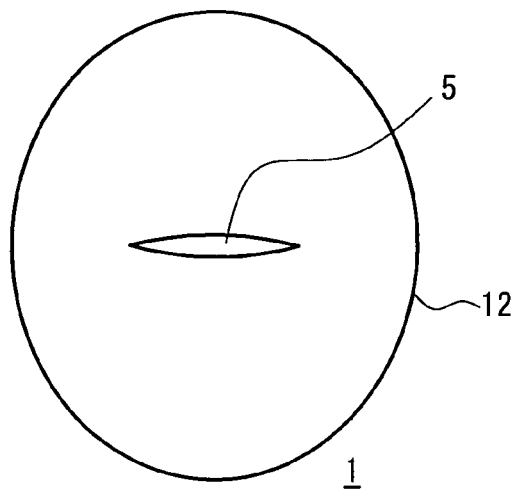
FIG. 4C is a bottom plan view thereof.
Figure 5:
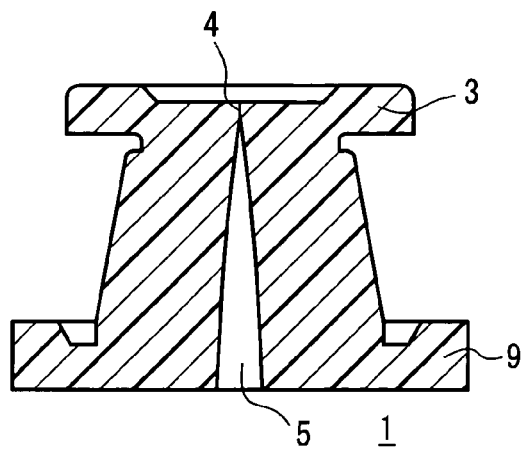
FIG. 5 is a cross sectional view along a line D-D in FIG. 4A.
Figure 6A:
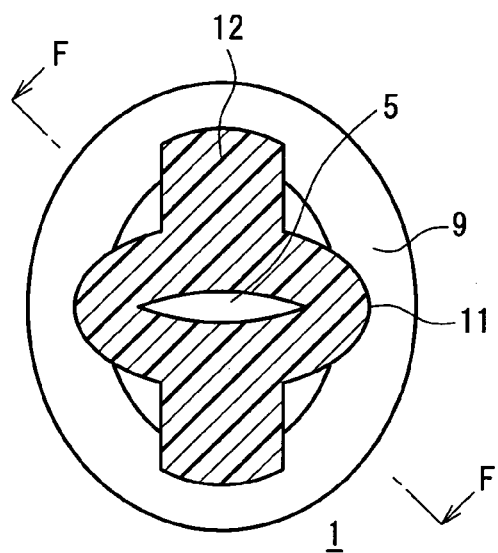
FIG. 6A is a cross sectional view along a line E-E in FIG. 4B.
Figure 6B:
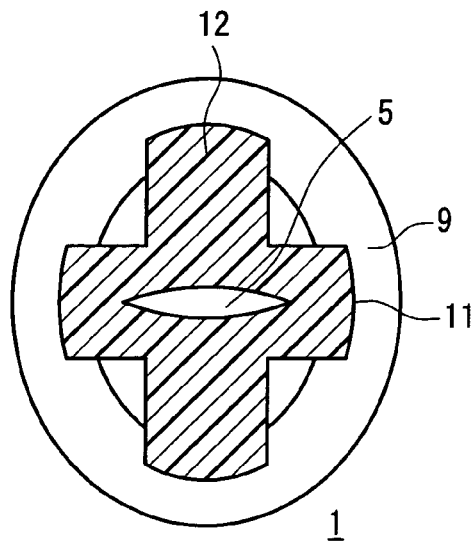
FIG. 6B is a cross sectional view of a modification example for the cross section shown in FIG. 6A.
Figure 7:
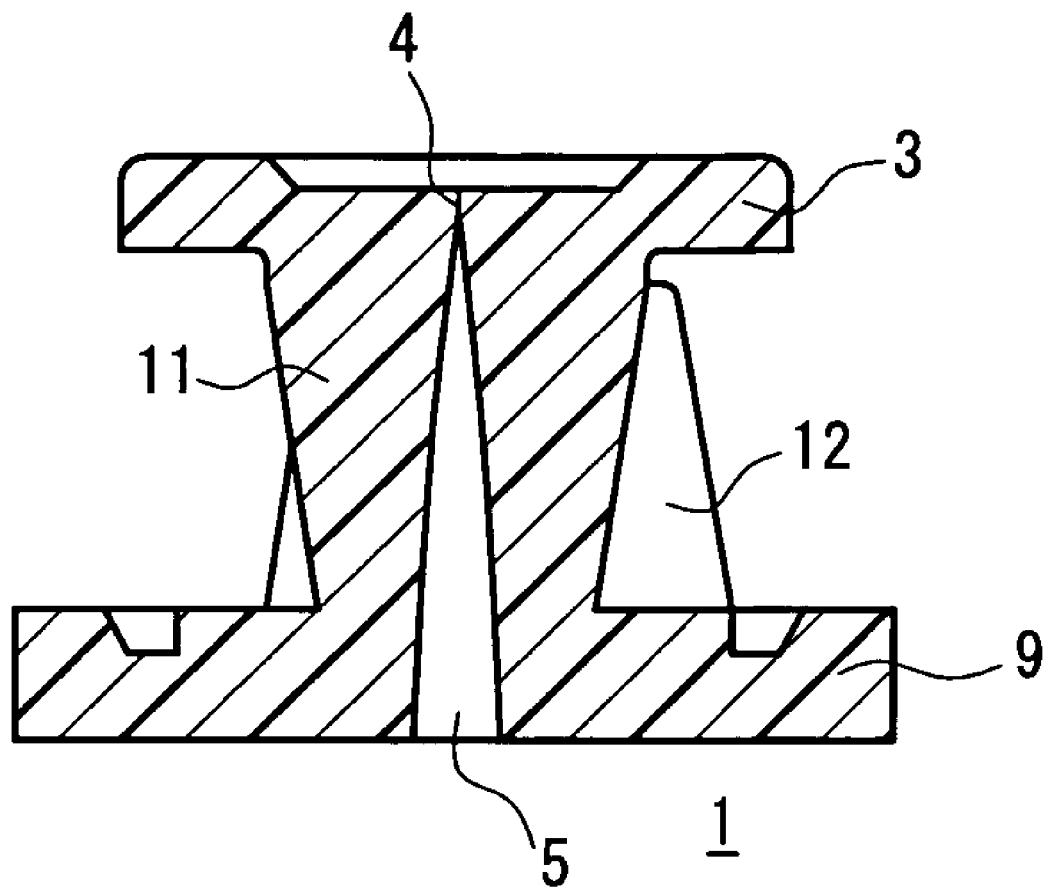
FIG. 7 is a cross sectional view along a line F-F in FIG. 6A.

The shape of the septum 1 is shown in FIGS. 3 to 7. FIG. 3 is a perspective view of the septum 1, when being held in the cavity 6a of the cover 6 in the needleless port shown in FIG. 1. FIG. 4A is a plan view of the septum 1, when not being mounted inside the cover 6 and being free. FIG. 4B is a cross sectional view thereof along a line C-C. FIG. 4C is a bottom plan view thereof. FIG. 5 is a cross sectional view of the septum 1 along a line D-D in FIG. 4A. FIG. 6A is a cross sectional view along a line E-E in FIG. 4B. FIG. 6B is a cross sectional view being modified from FIG. 6A. FIG. 7 is a cross sectional view of the septum along a line F-F in FIG. 6A.

As shown in FIG. 3, the septum 1 has a shape in which the main body 11 is sandwiched between the outer-end plate 3 and the inner-end plate 9. As shown in FIG. 4A, the outer-end plate 3 and the inner-end plate 9 each have an oval shape in a plan view. As shown in FIG. 6A, the main body 11 has an oval shape in a cross sectional view. The main body 11, as a whole, is in the shape of an inverse truncated oval cone. In other words, as shown in FIG. 7, the width of the main body 11, being measured in the direction orthogonal to the bore 5, gradually becomes smaller, from the outer-end plate 3 toward the inner-end plate 9. In addition, compression ribs 12 are provided on the sides of the main body 11, so that a compressive force can be applied to the main body 11 so as to close the bore 5. The detailed explanation on this configuration will be provided later.

As shown in FIGS. 4C, 5, and 6A, the bore 5 has, in a cross sectional view, a spindle shape whose major axis extends in the same direction as the major axis of the main body 11 in a cross sectional view. "A spindle shape" is defined as a shape formed of two arcs that are combined symmetrically so that both ends thereof are pointed. When the septum 1 is not disposed inside the cover 6 and is free, the bore 5 is not closed and fluid is allowed to go therethrough. Like the bore 5, the slit 4 extends in the same direction as major axis direction. Thus the bore 5 is continuous to the slit 4, extending therefrom.

The compression ribs 12 are provided at the both side ends of the main body 11 in the minor axis direction so as to extend along the axial direction of the bore 5. When the septum 1 is mounted in the cover 6, the main body 11 and the compression ribs 12 are positioned inside the cavity 6a of the cover 6.

Figure 8A:
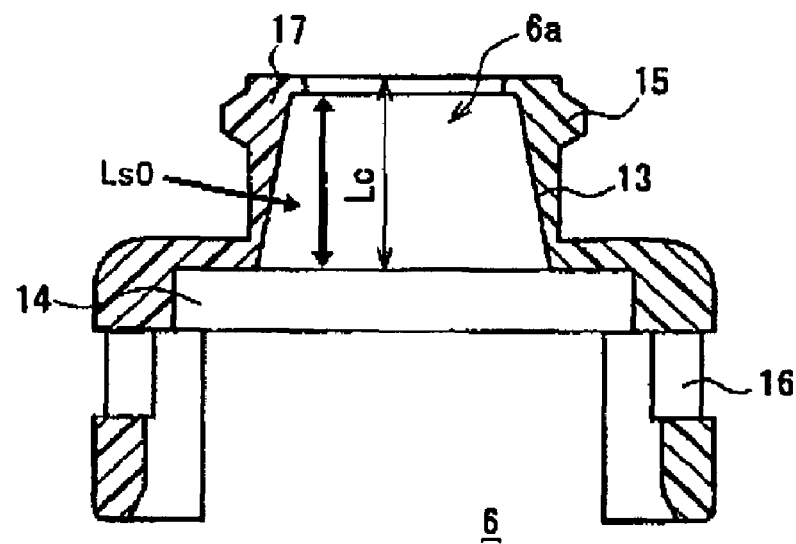
FIG. 8A is a cross sectional view of the cover in the needleless port in FIG. 1.
Figure 8B:
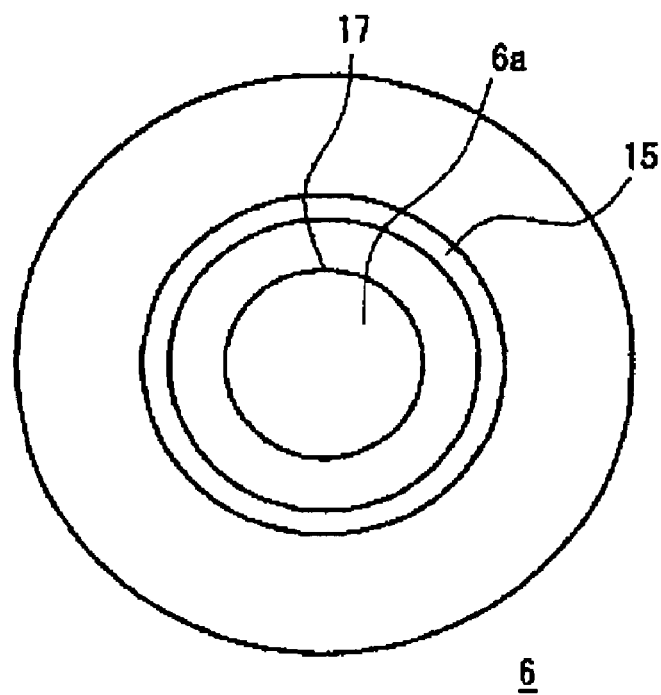
FIG. 8B is a plan view thereof.

FIG. 8A and FIG. 8B are a cross sectional view and a plan view, respectively, of the cover 6 of the present embodiment. FIG. 8A is a cross sectional view of the cover 6 along a line B-B in FIG. 1. FIG. 8B is a plan view thereof.

The cavity 6a of the cover 6 is, in a cross sectional view, in the shape of a perfect circle. The diameter of the cavity 6a gradually becomes larger from the outer end thereof (the upper side in the drawing) toward the inner end thereof, along the axial direction of the cavity 6a, so that the cavity 6a forms a tapered space 13, being tapered by the internal wall. A disc-shaped space 14 having a larger diameter than the tapered space and thereby forming a step is provided on the inner end side of the tapered space 13. The main body 11 and the compression ribs 12 of the septum 1 are to be positioned in the tapered space 13. The inner-end plate 9 is to be positioned in the disc-shaped space 14.

The diameter of the cavity 6a is smaller than each of the distance between the external surfaces of the pair of compression ribs 12 of the septum 1 and the major axis of the inner-end plate 9, which has an oval shape in a plan view. Consequently, in order to be disposed inside the cavity 6a, the septum 1 is to be pushed into the cavity 6a while being compressed. When the cover 6 is attached to the pedestal 7 while the septum 1 is in such a state, compressive forces from the cover 6, as shown with arrows in FIG. 2, constantly are applied to the septum 1. To the bore 5, particularly large compressive forces in such a direction so as close the bore 5 are applied from the compression ribs 12. Due to these compressive forces that are constantly applied to the septum 1, the bore 5 securely keeps dosed and achieves liquid-tightness, until an insertion member such as a luer is inserted there.

On the upper portion of the cover 6, a male screw-thread 15 is formed, so that the cover 6 can be engaged with a luer lock syringe. On the lower portion of the cover 6, an incision 16 is formed so that the cover 6 is to be fixed onto the pedestal 7 when the protrusion 7b of the pedestal 7 (see FIG. 2) is fitted into the incision 16.

As so far explained, compressive forces are constantly applied, via the compression ribs 12 and the inner-end plate 9, to the bore 5 in such a direction so as to close it. Accordingly, when an insertion member is not inserted, it is possible to ensure that the septum 1 has liquid-tightness. In addition, as explained above, the main body 11 has an oval shape in a cross sectional view, and the compression ribs 12 are provided at the both side ends of the main body 11 in the minor axis direction, providing an escape space between a part of the surface of the main body 11 and the internal wall of the cover 6. As a result, when an insertion member such as a luer is inserted through the slit 4 and the bore 5, the deformed parts of the septum 1 can enter into the escape space, allowing the inserting operation to be made easy. In order to make the escape space large enough, the cavity 6a of the cover 6 forms the tapered space 13 whose diameter gradually becomes larger from the outer end side toward the inner end side, which also contributes to achieving the ease of the insertion.

In addition, as mentioned above and as shown in FIG. 7, the main body 11 has, in a vertical cross sectional view (being sectioned at a plane parallel to the axis of the passageway) a shape of an inverse truncated cone. Due to this shape, it is possible to ensure that the escape space is large enough on the inner end side of the cavity 6a of the cover 6. In addition, since the main body 11 is wide enough on the outer end side, it is possible to have an escape space that is large enough while preventing a reduction of the anti-torsion strength of the septum 1.

As shown in FIG. 5 or FIG. 7 and as explained earlier, the septum 1 has both the slit 4 and the bore 5, whereby the insertion of an insertion member such as a luer is made easy due to the passageway, and liquid-tightness is achieved due to the slit.

On the contrary, in a case where the slit 4 is not provided, and only the bore 5 composes the passageway, when a pressure is applied, the top face of the septum 1 tends to be raised, so that the thrusting force from the cover 6 around the septum 1 weakens. Therefore the bore 5 opens up easily on the outer-end face, and there is a possibility of contamination by airborne bacteria and the like. Alternatively, in a case where the bore 5 is not provided, and only the slit 4 is provided, it is difficult to insert an insertion member such as a luer, because the resistance against the insertion is large. Further, it is difficult to hold an inserted insertion member at the appropriate position and to have the flow channel open. Furthermore, the formation of such a slit is difficult to perform, including positioning of the slit at the right position.

The slit 4 may be formed by cutting a slit into the material of the septum 1, with use of a knife, or the like. The bore 5 is formed in a molding process, by preparing a mold to be used for forming the septum 1 so that it has a shape corresponding to the bore 5. The structure in which the slit 4 and the bore 5 are formed continuously can be made in the following manner, for example: first, the septum 1 is molded with the bore 5 being molded at the same time, while leaving the portion where the slit 4 is to be made. Then, a slit is made, with a knife, into the portion where the slit 4 is to be positioned. In this process of making a slit, the knife can be put through the bore 5 to make the slit 4 so as to position the slit 4 with guidance by the bore 5. Thus, it is possible to make this process easy and accurate.

Alternatively, it is also possible to serve the septum 1 for practical use in a condition that the portion corresponding to the slit 4 is in an unpenetrated state. In other words, it is possible to break the unpenetrated portion with an insertion member when it is actually used. In such a case, the broken portion functions substantially in the same manner as the slit 4.

Normally, as shown in FIG. 6A, the main body 11 has, in a cross sectional view, an oval shape whose major axis extends in the same direction as the major axis of the bore 5 in a cross sectional view; however, the present invention is not limited to this configuration, and it is acceptable that the main body 11 has a shape as shown in FIG. 6B. In other words, it is sufficient if the size of a cross section of the main body 11 in the direction of the major axis of the bore 5 is larger than the size of the main body 11 in the direction of the minor axis of the bore 5. Thus, when the main body 11 is compressed via the compression ribs 12, a compressive force that is large enough to close the bore 5 will be applied.

In order to obtain the aforementioned effects with certainty, it is preferable that the ratio of the distance between the external surfaces of the compression ribs 12 to the inside diameter of the cover 6 and the ratio of the major axis of the inner-end plate 9 to the inside diameter of the cover 6 each be within a range of 1.05 to 1.4. Further, it is preferable that the ratio of dimension in a length direction of the main body 11 to the inside diameter of the cover 6 and the ratio of the minor axis of the inner-end plate 9 to the inside diameter of the cover 6 each be within a range of 0.8 to 1.0.

As shown in FIGS. 4B, 5, and 7, the bore 5 is formed so that in a vertical cross section, the length in the minor axis and the length in the major axis of the spindle shape gradually become larger from the interface between the bore 5 and the slit 4 toward the bottom of the septum 1. In other words, the bore 5 is formed so that the size of the open area gradually becomes larger toward the inner-end plate 9 of the septum 1.

With these configurations, it is possible to avoid a leakage, of a residual fluid when a luer or the like is taken out as well as to avoid stagnation of fluid. More specifically, as mentioned above, compressive forces from the cover 6 are constantly applied to the septum 1 via the compression ribs 12 as shown with the arrows in FIG. 2. Since the compressive forces are applied to the bore 5 evenly, the closing force is stronger on the outer end side of the bore 5 where the area size of the cross section is smaller. Thus, the fluid that tries to remain in the bore 5 is to be sequentially pushed out toward the inner end side of the septum 1. As a result, the fluid is removed from the end of the bore 5 on the inner end side of the septum 1. The shape of the cavity 6a of the cover 6 also contributed to the action of removing the fluid because of the tapered space 13 whose diameter gradually becomes larger from the outer end side toward the inner end side. More specifically, the compressive forces applied to the main body 11 of the septum 1 from the internal wall of the tapered space 13 is larger on the outer end side than on the inner end side. Therefore the residual fluid tends to receive forces such that it is pushed toward the inner end side.

It is possible that the outer-end plate 3 of the septum 1 has, in a cross sectional view, an oval shape as shown in FIG. 4A, or alternatively a circular shape. There is no limitation about the shape of the outer-end plate 3. It is preferable if one or more of the following conditions is satisfied: the outer-end plate 3 has an area size that is larger than an area size of the cavity 6a of the cover 6 at the outer end portion, in a cross sectional view; the outer-end plate 3 has a thicker portion; and the outer-end plate 3 has the surface depression 2 that serves as guidance when a luer or the like is inserted.

If the area size of the outer-end plate 3 was not larger than the area size of the cavity 6a of the cover 6 at the outer end portion, there is a possibility that the outer-end plate 3 might fall inside the cover 6 when, for example, a luer is inserted.

The thicker portion has an effect of preventing the outer-end plate 3 from being drawn into the cover 6 when a luer or the like is inserted into the slit 4. The following explains the meaning of "the thicker portion" with reference to FIG. 4B. In FIG. 4B, t1 refers to the thinner portion and the t2 refers to the thicker portion. The thickness t2 of the thicker portion corresponds to the thickness of the outer-end plate 3. The thickness t1 of the thinner portion corresponds to the thickness of the portion where the thickness is the smallest, that is the distance between the edge portion at the boundary between the external surface of the main body 11 and the external surface of the outer-end plate 3 and the edge portion of the surface depression 2. By providing the septum 1 with the thinner portion 1, which is thinner than the thicker portion t2, the septum 1 is easily deformed at the thinner portion t1, so that an insertion member is easily inserted because of reduced resistance against the insertion.

Further, by providing the septum 1 with the surface depression 2, it is possible to guide a luer or the like into the slit 4. Also, in a case where the contained liquid has leaked in a process of taking out the luer or the like, it is easy to clean it off since the liquid is kept in the depression.

The septum 1 is mounted in the cover 6, while expanding the main body 11. In other words, the length Ls0 (see FIG. 4B) of the main body 11 of the septum 1, as not being mounted in the cover 6, is smaller than the length Lc (see FIG. 8B) of the part of the cover 6 used for holding the main body 11. With this configuration, even when the outer-end plate 3 of the septum 1 is pressed outward by the pressure from inside the flow channel, a force of restoring it to the original state acts on the upper-end face of the cover 6. Also, since the outer-end plate 3 is pulled toward inside, a force operates so as to close and seal the slit on the surface of the outer-end plate 3. In addition, since the surface is depressed smoothly, it is further easier to stick an insertion member into the slit.

It is preferable to arrange the sizes of the septum 1 and the cover 6 so that the expansion ratio is within a range of 5% to 40%, where the expansion ratio is calculated by dividing the expanded length of the septum 1 as being held in the cover 6 by the length Lc of the part of the cover 6 used for holding the main body 11.

It is not necessary that the main body 11 of the septum 1 is expanded when it is mounted in the cover 6. The reason is that since the cavity 6a of the cover 6 has a tapered space in which the internal wall is tapered so that the diameter thereof gradually becomes larger toward the inner end side, even if a force that presses the septum 1 outward is applied due to the pressure from inside the flow channel, another force that acts against this force is applied from the tapered surface of the cavity 6a to the septum 1.

As mentioned above, because of the configuration wherein the septum 1 has the slit 4 in the outer end portion thereof as well as the bore 5 as an extended continuum of the slit 4, it is possible to make it easier to insert an insertion member and achieve the liquid-tightness. In addition, it is preferable to make a configuration that satisfies the following: the ratio Ls/Lh is within the range expressed by the formula (1), where Ls represents the depth of the slit 4 in the direction of the passageway, and Lh represents the height of the septum 1, as shown in FIG. 4B.

$$0.04 \leq Ls/Lh \leq 0.60 \quad (1)$$

When the Ls/Lh is smaller than 0.04, there is a possibility that the bore 5 is formed as a through hole due to variations in the manufacturing process, for example. Also, when the internal pressure is applied, the septum opens up more easily on the outer end portion thereof. On the contrary, when Ls/Lh is larger than 0.60, it is difficult to insert an insertion member, hold an insertion member, and form the slit 4.

Further, it is preferable that the depth Ls of the slit 4 is within the range expressed by the formula (2).

$$0.2 \text{ mm} \leq Ls \leq 3.0 \text{ mm} \quad (2)$$

When the depth Ls of the slit 4 is smaller than 0.2 mm, there is a possibility that the outer-end face of the septum 1 opens up when a pressure is applied. When the depth Ls of the slit 4 is larger than 3.0 mm, it is difficult to form the slit. Further, it is difficult to maintain the passageway because the open area is small.

As shown in FIG. 1B, the annular rib 8 of the pedestal 7 engages with the bottom of the septum 1. By providing the annular rib 8 with such an configuration, it is possible to prevent the liquid from leaking between the pedestal 7 and the septum 1.

The surface of the inner-end plate 9 of the septum 1 is flat. With this configuration, there is no dead space inside the port, eliminating the possibility of causing bubbles or the like to remain in a dead space.

A material of the septum 1 should have rubbery resilience in general, and preferably has the stiffness of 20 to 60 measured according to the JIS-A. Specific examples of the material are synthetic rubber such as silicon rubber, isoprene rubber, butyl rubber, nitrile rubber and thermoplastic elastomer.

The characteristics required for the material of the septum 1 are as follows: slipperiness (effective in insertion and anti-abrasion); resilience (effective in restoration); strength (effective in anti-abrasion and durability); flexibility (effective in insertion). A material that has all of these characteristics in a good balance is, for example, silicon rubber with stiffness 30 to 50 high tear strength) according to the JIS-A stiffness standard.

A material of the cover 6 should have appropriate hardness in order to hold the septum 1 and an insertion member. For example, desirable materials are polyacetal, polypropylene, polyethylene, polyamide, polyethylene terephthalate, polybutylene terephthalate, polycarbonate, or the like.

Figure 9:
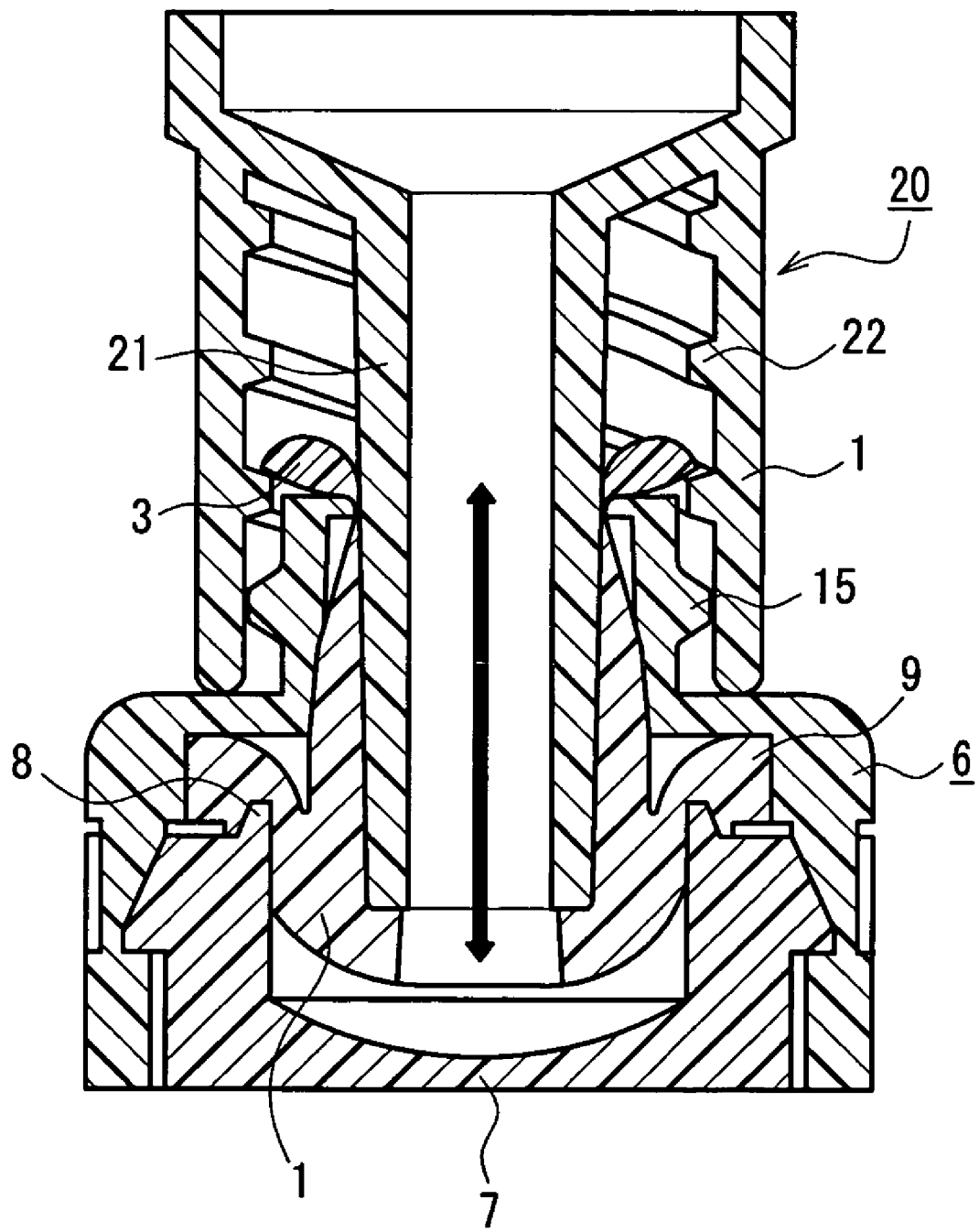
FIG. 9 is a cross sectional view of the needleless port shown in FIG. 1, into which an insertion member is inserted.

FIG. 9 is a cross sectional view of the needleless port of the embodiment of the present invention, into which a luer lock syringe 20 is inserted. As the luer lock syringe 20 is being inserted, the septum 1 is pushed downward by the luer 21 so as to draw the outer-end plate 3 and the thicker portion of the outer-end plate 3 is caught by the rim inside the upper portion of the cover 6. When the luer 21 is further pushed in, the thinner portion, which is positioned more inward than the thicker portion is, is pulled and expanded. The inner-end plate 9 that has been compressed by the cover 6 then will be pushed out downward at the bottom of the septum 1. Thus, the compressive force by the cover 6 acting on the septum 1 is released, so that the bore 5 opens.

When the luer lock syringe 20 is rotated as being inserted, the male screw-thread 15 in the cover 6 becomes engaged with the female screw-thread 22 in the luer lock syringe 20.

When the luer lock syringe 20 is pulled out, the septum 1 is restored to its original shape due to the actions of the thicker portion of the inner-end plate 9 and the annular rib 8. It this state, at the bottom of the septum 1, the compressive force by the cover 6 acts again on the inner-end plate 9 of the septum 1, and thereby the bore 5 closes.

Figure 10A:
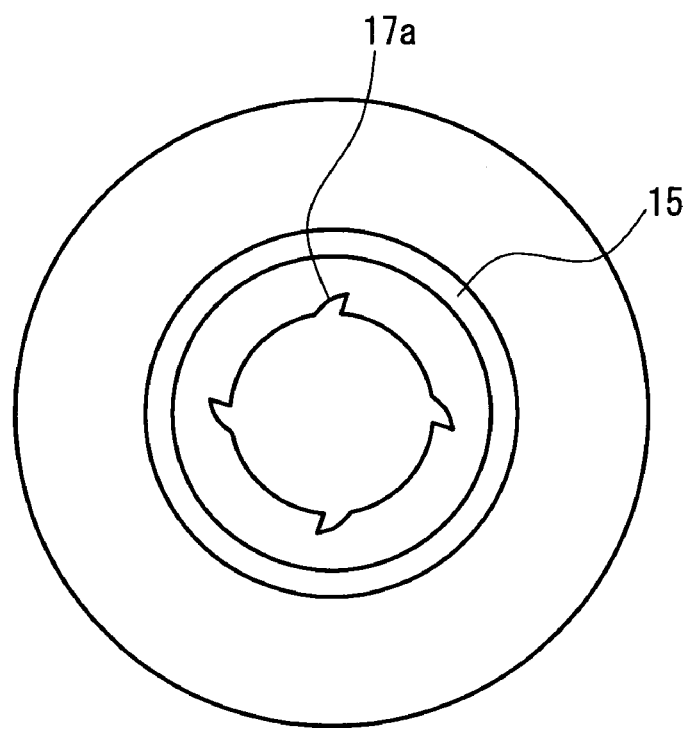
FIGS. 10A and 10B are plan views, each showing a modification example of the cover in the needleless port in FIG. 1.
Figure 10B:
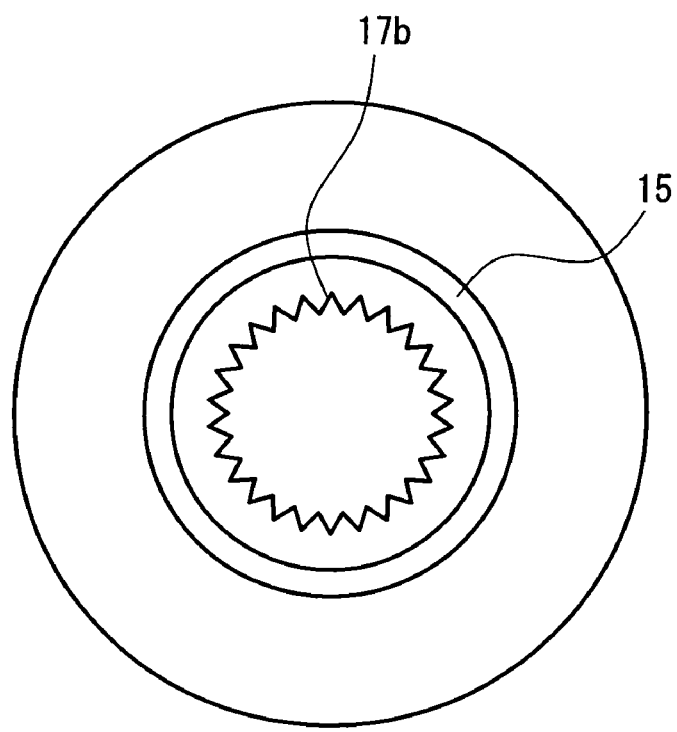

When the luer lock syringe 20 is rotated as being inserted, a twisting force may act on the septum 1 excessively so as to cause the septum 1 to be get twisted, depending on the properties of the material of the septum. In such a case, there is a possibility that the passageway is blocked, or the septum 1 cannot be restored to its original shape after the luer lock syringe 20 is taken out. In order to solve such a problem, it is effective to provide, as shown in FIGS. 10A and 10B, indents 17a or indents 17b on inside of the circumferential portion of the cover 6. When the indents 17a or 17b are provided, as the luer 21 is inserted, the deformed parts of the septum 1 enter into the indents 17a or 17b. Thus, even when the luer lock syringe 20 is rotated, due to retaining force by the indents 17a or 17b, the septum 1 will not be twisted, and it is possible to maintain the passageway.

The indents may be in the shapes shown in FIG. 10A, projecting in the direction of rotation, or in the shapes shown in FIG. 10B, like gears with a number of indents, or any other shapes.

Figure 11:
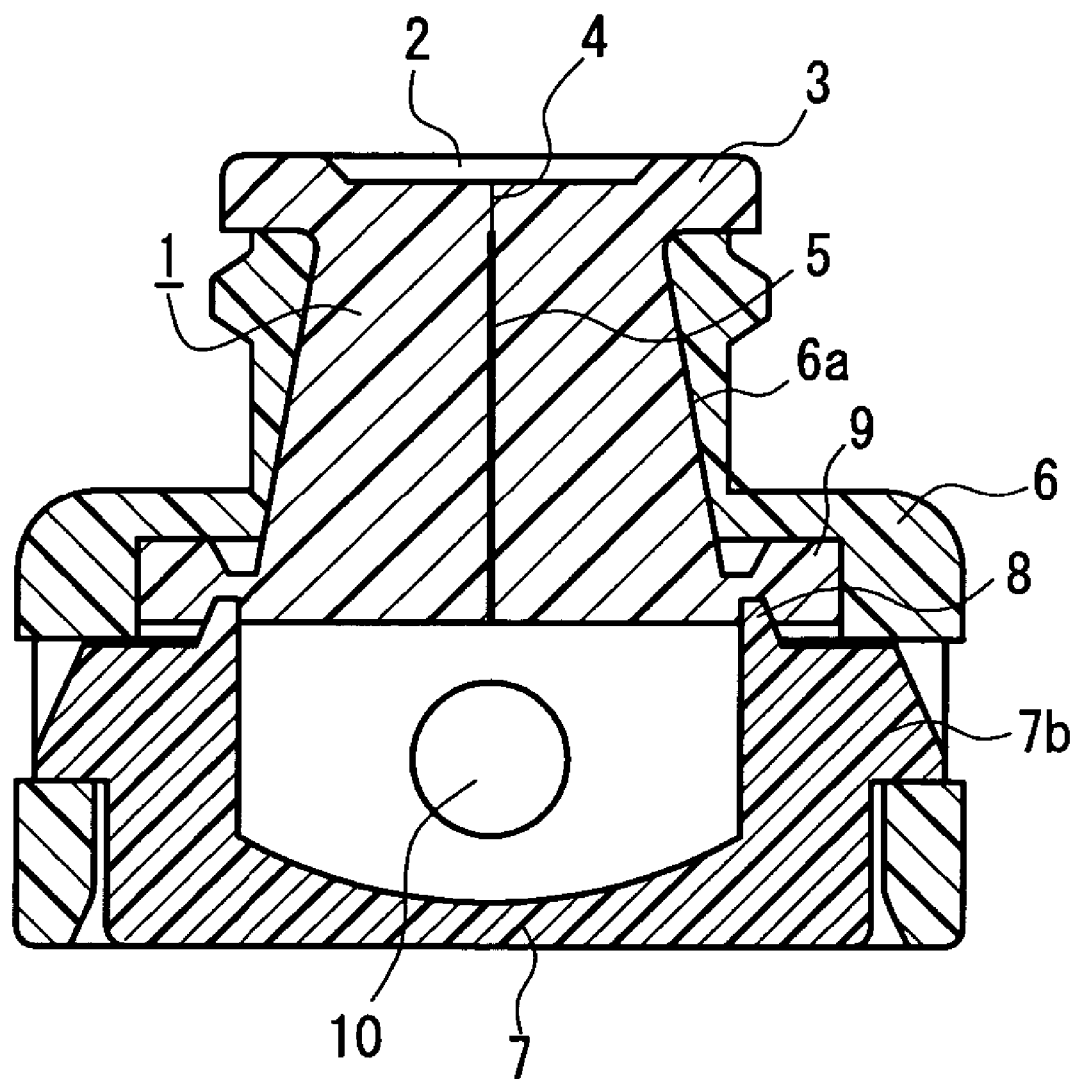
FIG. 11 is a cross sectional view of a modification example of the cover to be included in the needleless port of the embodiment of the present invention.

FIG. 11 shows a modification example in which the structures of the cover 6 and the septum 1 are modified from the example mentioned above. In the example mentioned above, the cover 6 has a projection at inside of the circumferential portion on the outer end side thereof as shown in FIGS. 1, 8A, and so on. As shown in FIG. 4B, the septum 1 has, in correspondence with this projection, a depression on the external surface at the boundary between the main body 11 and the outer-end plate 3. This combination of the projection and the depression is arranged in order to make sure the effect of holding the septum 1 inside the cover 6; however, this configuration is not required. In other words, as shown in FIG. 11, it is also possible, alternatively, that the internal wall of the cover 6 and the external wall of the main body 11 of the septum 1 are each arranged to be smooth.

Even with this alternative configuration, the effect of holding the septum 1 inside the cover 6 is sufficient, due to the configurations in which the septum 1 has the outer-end plate 3 and the inner-end plate 9, as well as the cavity 6a of the cover 6 is tapered so that the inside diameter gradually becomes larger toward the inner end side. Also, like the configuration shown in FIG. 1 and the like, the thickness of the thinner portion is smaller than the thickness of the outer-end plate 3, in which the thinner portion is the smallest thickness portion positioned between the edge portion at the boundary between the external surface of the main body 11 and the external surface of the outer-end plate 3 and the edge portion of the surface depression 2.

Figure 12A:
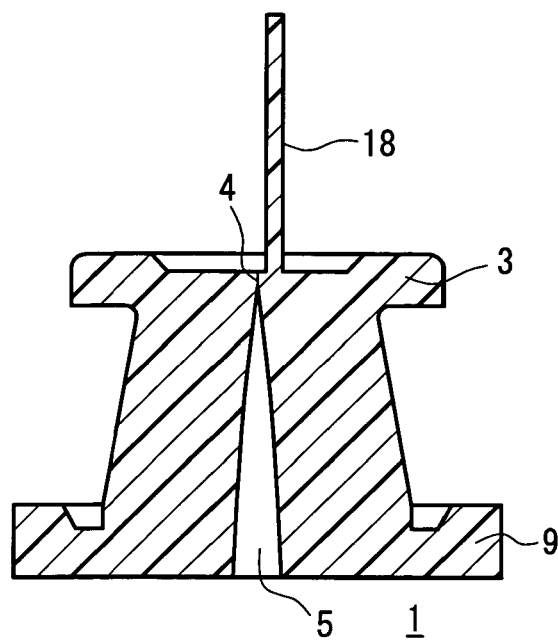
FIGS. 12A and 12B are cross sectional views, each showing a part of the processes in a method of manufacturing the needleless port of the embodiment of the present invention.
Figure 12B:
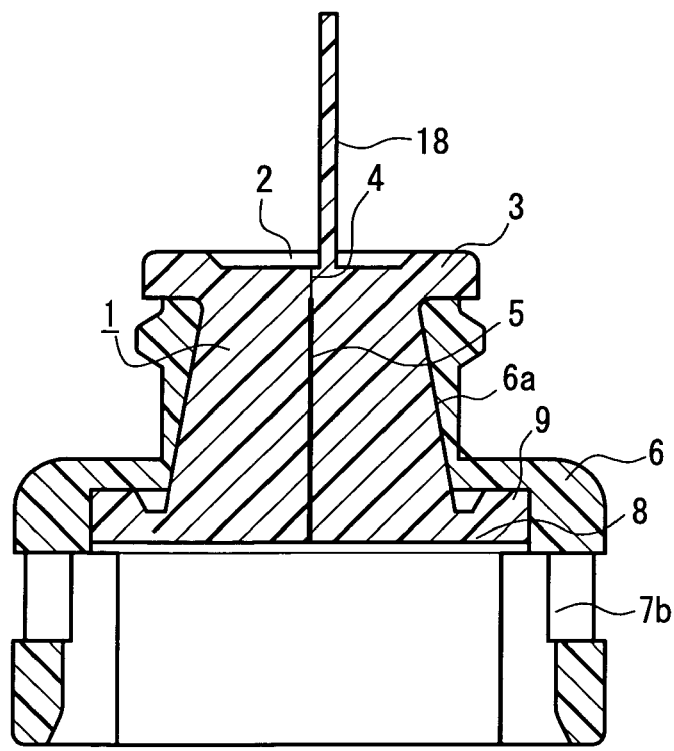

The following describes a method of manufacturing a needleless port of an embodiment of the present invention, with reference to FIGS. 12A and 12B. FIGS. 12A and 12B show steps of mounting the septum 1 in the cavity 6a of the cover 6.

As shown in FIG. 12A, when the septum 1 is manufactured, a slender stick-like knob 18 is formed on the upper-end face thereof. The basal portion of the stick-like knob 18 is displaced from the position of the slit 4. In order to mount the septum 1 in the cavity 6a, the stick-like knob 18 is put through into the cavity 6a of the cover 6 from the inner end side thereof toward the outer end side thereof as shown in FIG. 12B. Then the stick-like knob 18 is pulled while the septum 1 is pushed into the cavity 6a. After that, the stick-like knob 18 is cut off at its basal portion. By using the stick-like knob 18 like this, it is easy to place the septum 1.

Figure 13A:
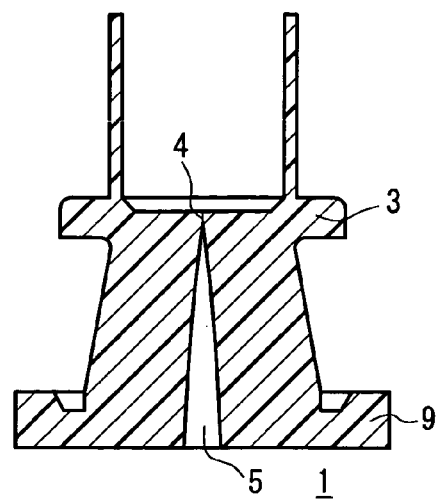
FIGS. 13A, 13B, 13C are cross sectional views, each showing a part of the processes in another manufacturing method of the needleless port of the embodiment of the present invention.
Figure 13B:
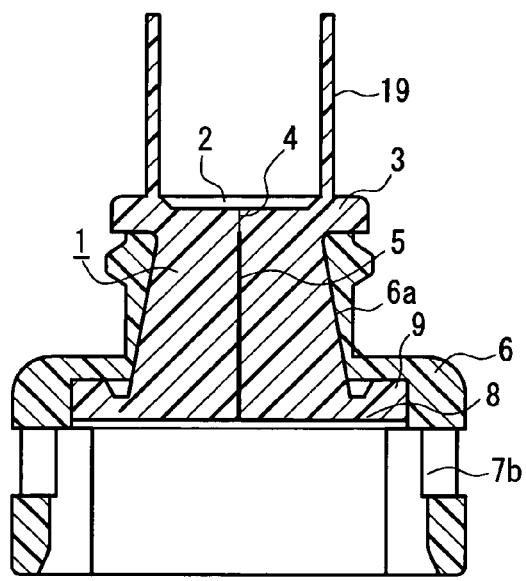
Figure 13C:
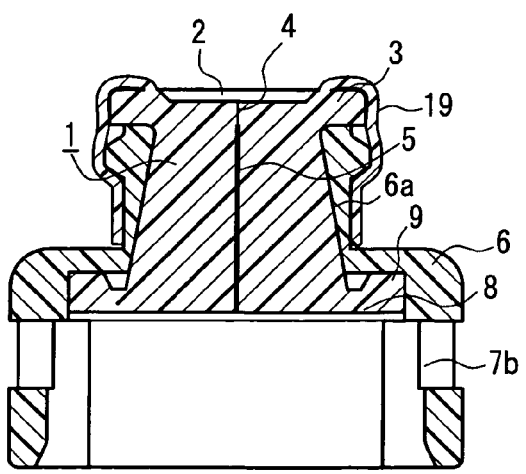

The other methods of manufacturing the needleless port will be described below, with reference to FIGS. 13A, 13B, and 13C. FIGS. 13A, 13B, 13C also show steps of mounting the septum 1 in the cavity 6a of the cover 6.

As shown in FIG. 13A, when the septum 1 is manufactured, a tube-like knob 19 is formed on the upper-end face thereof. The basal portion of the tube-like knob 19 is positioned at the thicker portion of the outer-end plate 3 around the surface depression 2 so that the basal portion of the tube-like knob 19 surrounds the slit 4. In order to mount the septum 1 in the cavity 6a, the tube-like knob 19 is put through into the cavity 6a of the cover 6 from the inner end side thereof toward the outer end side thereof, as shown in FIG. 13B. Then, the tube-like knob 19 is pulled while the septum 1 is pushed into the cavity 6a. By using the stick-like knob 19 like this, it is easy to place the septum 1.

Next, as shown in FIG. 13C, the tube-like knob 19 is turned inside out as shown in FIG. 13C, so as to cover the external wall of the cover 6. With this configuration, it is possible to suppress the twisting of the septum 1 by the twisting force that acts when the luer lock syringe 20 is rotated as being inserted, as shown in FIG. 9. Alternatively, it is also acceptable to cut off the tube-like knob 19 at the basal portion, instead of turning it inside out.

INDUSTRIAL APPLICABILITY

According to the needleless port of the present invention, a dead space causing a residual fluid is suppressed to be formed inside the passageway in the septum and the slit provided on the surface of the septum does not open easily, even when a pressure is applied. Also since the needleless port has a versatile structure, it is possible to apply it to various medical devices.

The invention claimed is:

1. A needleless port comprising: a pedestal that forms a part of a flow channel and has an opening to the flow channel; a cover that is engaged with the pedestal at a position corresponding to the opening and has a cavity that opens to exterior at a predetermined distance from the opening; and a septum that is held in the cavity and is made of a resilient material with a passageway for allowing an insertion member to be inserted from the exterior to the opening, wherein the septum comprises a main body that extends from an inner end on the pedestal side toward an outer end on the exterior side of the cavity of the cover, with the passageway being formed between an inner-end face and an outer-end face thereof, and compression ribs provided on an external surface of the main body, the main body has a cross section in a direction orthogonal to the passageway of a shape having an external dimension in a length direction larger than that in a breadth direction, the passageway includes a slit and a bore, the slit originating at the outer end face of the main body and extending in the same direction as the length direction so as to have a predetermined depth from the outer-end face of the main body, and the bore extending from the slit to the inner-end face of the main body prior to insertion of the insertion member and having a lateral section of a spindle shape whose major axis extends in the same direction as the length direction, the compression ribs are provided at the both side ends of the main body in the breadth direction so as to extend along the axial direction of the passageway, the cavity of the cover has a circular cross section whose diameter is smaller than a distance between the external surfaces of the compression ribs, and with the septum being held inside the cavity, a space is formed between the external surface of the main body at a part without the compression ribs and an internal wall of the cover, and the bore is closed by a compressive force applied from the internal wall of the cover to the septum via the compression ribs.

2. A needleless port comprising: a pedestal that forms a part of a flow channel and has an opening to the flow channel; a cover that is engaged with the pedestal at a position corresponding to the opening and has a cavity that opens to exterior at a predetermined distance from the opening; and a septum that is held in the cavity and is made of a resilient material with a substantial passageway for allowing an insertion member to be inserted from the exterior to the opening, wherein the septum comprises a main body that extends from an inner end on the pedestal side toward an outer end on the exterior side of the cavity of the cover, with the substantial passageway being formed between an inner-end face and an outer-end face thereof, and compression ribs provided on an external surface of the main body, the main body has a cross section in a direction orthogonal to the substantial passageway of a shape having an external dimension in a length direction larger than that in a breadth direction, the substantial passageway includes an unpenetrated region and a bore, the unpenetrated region originating at the outer end face of the main body so as to have a predetermined depth from the outer-end face of the main body, and the bore extending from the unpenetrated region to the inner-end face of the main body prior to insertion of the insertion member and having a lateral section of a spindle shape whose major axis extends in the same direction as the length direction, the compression ribs are provided at the both side ends of the main body in the breadth direction so as to extend along the axial direction of the substantial passageway, the cavity of the cover has a circular cross section whose diameter is smaller than a distance between the external surfaces of the compression ribs, and with the septum being held inside the cavity, a space is formed between the external surface of the main body at a part without the compression ribs and an internal wall of the cover, and the bore is closed by a compressive force applied from the internal wall of the cover to the septum via the compression ribs.

3. The needleless port according to claim 1, wherein the septum has, on an inner end of the main body, an inner-end plate that has an oval shape whose major axis extends in the same direction as the breadth direction of the main body, a length of a major axis of the inner-end plate is larger than an inside diameter of the internal wall of the cover, and with the septum being held inside the cavity, a compressive force acting in the major axis direction is applied from the cover to the inner-end plate.

4. The needleless port according to claim 1, wherein the septum has, around an outer end of the main body, an outer-end plate that is exposed to outside of the cover and is larger in size than an inside diameter of the cover at an Outer end of the cover.

5. The needleless port according to claim 1, wherein lengths in the major axis and the minor axis of the section of the bore gradually become larger from the outer-end face of the main body toward the inner-end face of the main body.

6. The needleless port according to claim 1, wherein the septum has, on an outer end thereof, a surface depression portion which is formed at a central area to be substantially level and depressed in relation to an area surrounding the central area.

7. The needleless port according to claim 1, wherein a surface of the outer-end plate is flat.

8. The needleless port according to claim 1, wherein a length LsO of the main body in a state in which the septum is not mounted inside the cover is smaller than a length Lc of the cover at a portion for holding the main body therein.

9. The needleless port according to claim 8, wherein with the septum being held inside the cover, an expansion ratio is within a range of 5% to 40%, the expansion ratio being calculated by dividing an expanded length of the septum by the length Lc.

10. The needleless port according to claim 1, wherein the internal wall of the cover forming the cavity is tapered so that the diameter of the cavity section gradually becomes smaller from the inner end thereof toward the outer end thereof along an axis of the cavity.

11. The needleless port according to claim 1, wherein a ratio of the distance between the external surfaces of the compression ribs to the inside diameter of the cover and a ratio of the length in the major axis of the inner-end plate to the inside diameter of the cover are each within a range of 1.05 to 1.4.

12. The needleless port according to claim 11, wherein a ratio of a dimension in the breadth direction of the main body to the inside diameter of the cover and a ratio of a minor axis of the inner-end plate to the inside diameter of the cover are each within a range of 0.8 to 1.0.

13. The needleless port according to claim 1, wherein an area size of a cross section of the space between the external surface of the main body at the portion without the compression ribs and the internal wall of the cover gradually becomes larger from an outer end of the cover toward an inner end of the cover.

14. The needleless port according to claim 1, wherein a ratio of the predetermined depth of the slit to a height of the main body of the septum is within a range of 0.04 to 0.60, the predetermined depth being measured in a direction of the passageway.

15. The needleless port according to claim 1, wherein the predetermined depth of the slit measured in a direction of the passageway is within a range of 0.2 mm to 3.0 mm.

16. The needleless port according to claim 3, wherein an annular rib is provided around the opening of the pedestal, the annular rib projecting toward the cover, and the inner-end plate of the septum is sandwiched between the internal wall of the cover and the annular rib so that the annular rib engages with a bottom surface of the inner-end plate, thereby establishing liquid-tightness.

17. The needleless port according to claim 16, wherein the internal wall of the cover has one or more indents that are to be engaged with an external surface of the septum.

18. The needleless port according to claim 1, wherein an inner peripheral portion at an outer end of the cover is chamfered.

19. The needleless port according to claim 1, wherein a material of the septum is one of silicon rubber, isoprene rubber, butyl rubber, nitrile rubber and thermoplastic elastomer.

20. A method of manufacturing the needleless port according to claim 1, wherein in a process of molding the septum, a knob is formed on the outer-end face of the septum at a position being displaced from a position of the slit, and when mounting the septum inside the cavity, the knob is put through the cavity from the inner end thereof to the outer end thereof, and thereafter the knob is pulled while the septum is pushed into the cavity.

21. The manufacturing method according to claim 20, wherein after the septum is mounted inside the cavity, the knob is cut off at a basal portion thereof.

22. The manufacturing method according to claim 20, wherein the knob is lube-shaped, with the basal portion thereof being formed so as to surround the slit, and after the septum is pushed into the cavity, the tube-shaped knob is turned inside out so as to cover an external surface of the cover.

* * * * *